United States Patent [19]  [11]  4,290,974
Bouillon et al.  [45]  Sep. 22, 1981

[54] OXYBENZYLIDENE-BORNANONES, THEIR PREPARATION AND THEIR USE IN COSMETICS

[75] Inventors: Claude Bouillon, Eaubonne; Charles Vayssie, Villepinte, both of France

[73] Assignee: L'Oreal, Paris, France

[21] Appl. No.: 56,262

[22] Filed: Jul. 10, 1979

[30] Foreign Application Priority Data

Jul. 11, 1978 [FR] France .................. 78 20701

[51] Int. Cl.³ .................. C07C 143/36; C07C 49/573; C07C 49/563
[52] U.S. Cl. .................... 260/511; 260/508; 260/509; 260/340.3; 260/340.5 R; 260/501.19; 260/501.21; 260/465 K; 542/449; 560/14; 560/53; 562/462; 562/463; 564/428; 564/443; 564/287; 568/327; 568/442; 568/313
[58] Field of Search .................. 260/590 B, 570, 51 A, 260/511, 509, 590 FB, 340.7, 340.9 R, 340.3, 508, 510, 340.3, 340.5 R, 501 R; 424/59, 60; 562/401, 429, 462, 463; 560/53, 14; 568/327; 542/449; 364/428

[56] References Cited

U.S. PATENT DOCUMENTS

| 3,715,875 | 12/1968 | Luetho et al. | 424/59 |
| 3,749,732 | 7/1973 | Rody et al. | 424/59 |
| 3,781,417 | 12/1973 | Welters et al. | 424/59 |
| 3,821,307 | 6/1974 | Hoch | 260/590 B |
| 4,061,730 | 12/1977 | Kalopissis et al. | 424/59 |
| 4,165,336 | 8/1979 | Bouillon et al. | 260/511 |
| 4,165,337 | 8/1979 | Bouillon et al. | 260/511 |

FOREIGN PATENT DOCUMENTS

| 2407733 | 8/1974 | Fed. Rep. of Germany | 260/590 B |
| 2309523 | 7/1973 | France | 424/59 |
| 2199971 | 9/1973 | France | 424/59 |
| 2282426 | 2/1974 | France | 424/59 |
| 2282426 | 3/1976 | France | 260/590 B |

Primary Examiner—Natalie Trousof
Assistant Examiner—James H. Reamer
Attorney, Agent, or Firm—Fleit & Jacobson

[57] ABSTRACT

The invention relates to oxybenzylidenebornanones which correspond to the general formula:

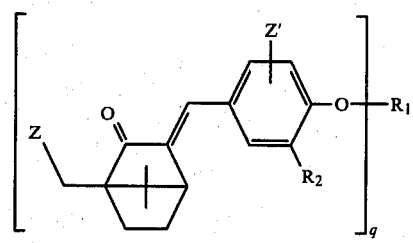

in which Z and Z' denote hydrogen or a radical SO₃H, at least one of the two radicals Z and Z' denoting hydrogen, $R_1$ denotes hydrogen, an alkyl radical having 2 to 18 carbon atoms, an alkenyl radical having 3 to 18 carbon atoms, a radical $-(CH_2CH_2O)_nH$,

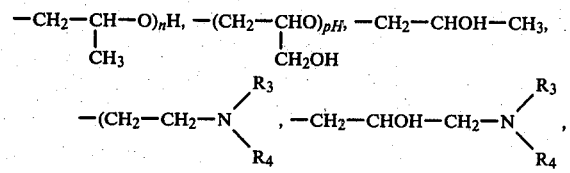

$-(CH_2)_mCO_2R$, in which R denotes H or an alkyl radical, $-(CH_2)_3SO_3H$ or a divalent radical $-(CH_2)_m$ or $-CH_2-CHOH-CH_2$, m having the values 1 to 10, n having the values 1 to 20 and p having the values 1 to 6, and $R_3$ and $R_4$ representing hydrogen or an optionally branched or hydroxylic alkyl radical, or forming an aminoaliphatic heterocyclic ring with the nitrogen atom, $R_2$ denotes a hydrogen atom, an alkoxy radical or a divalent radical —O— bonded to the radical $R_1$ if the latter is also divalent, and q denotes 1 or 2; if q has the value 2, $R_1$ is a divalent radical, and, if $R_1$ denotes hydrogen, $R_2$ also denotes hydrogen. These compounds can be used in cosmetic compositions for providing protection against actinic rays.

10 Claims, No Drawings

OXYBENZYLIDENE-BORNANONES, THEIR PREPARATION AND THEIR USE IN COSMETICS

DESCRIPTION

The present invention relates to a new class of oxybenzylidene-bornanones, and also to the process for their preparation and to their use in the field of cosmetics.

The compounds of the invention possess remarkable absorption properties over a very broad range of actinic radiation, which renders them particularly suitable for the preparation of cosmetic compositions intended to preserve the human epidermis, in particular in the case of delicate epidermides.

It is known that the sun filters or sunscreens usually employed are chosen from amongst compounds of which the absorption is a maximum in the wavelength zone between 285 and 315 nanometers (nm), in which zone prolonged exposure causes erythema and then sunburn on the human epidermis.

The use of compounds which are active in the above-mentioned wavelength zone is already known. Thus French Patent No. 2,199,971 discloses benzylidene-camphor derivatives containing a quaternary ammonium radical on the benzene nucleus in the para-position relative to the bornylidene radical for this purpose. French Patent No. 2,282,426 discloses benzylidene-camphor derivatives sulphonated on the methyl radical in the α-position relative to the carbonyl radical, or on the benzene nucleus, for this purpose.

Certain filters having a broad absorption zone, such as 2,4-dihydroxybenzophenone, are also known, but their absorption capacity is relatively low and their effectiveness is very mediocre.

UV radiation having wavelengths of between 285 and 315 nanometers plays a predominant part in the production of the erythema caused by the sun; it is accepted that this radiation is responsible for the latter to an extent of the order of 90%. It is for this reason that a specific protection in this radiation zone has been particularly sought hitherto.

However, it is becoming increasingly apparent that protection in the abovementioned wavelength zone is insufficient as regards delicate skin, in particular fair skin, which possesses a particular sensitivity to solar radiation or which does not easily become sunburnt, even after repeated exposure to the sun.

Moreover, radiation which has wavelengths of between 315 and 340 nanometers (known by the designation short UV-A), and the intensity of which in the solar spectrum is very much greater than that of radiation having wavelengths of between 285 and 315 nanometers (known by the designation UV-B), plays an important part in the sensitisation to the sun of the "skin surface", that is to say a surface of the epidermis type, by assisting the initiation of the erythematous reaction or by amplifying this reaction in certain subjects.

The object of this invention is to provide a family of compounds which strongly absorb ultraviolet radiation over a broad range including wavelengths of between 290 and 340 nanometers, in particular between 315 and 340 nm, which compounds also have good solubility in the usual cosmetic solvents, good light-stability and also good chemical stability, in particular in contact with perspiration.

This invention firstly provides the 3-(para-oxybenzylidene)-bornan-2-ones of the general formula I:

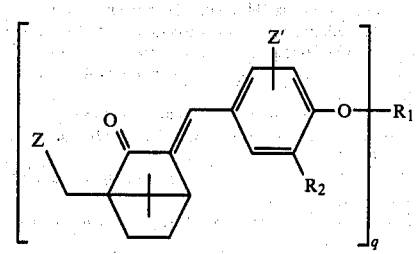

in which: Z and Z' respectively denote a hydrogen atom or a radical $SO_3H$, or a salt of this sulphonic acid with an inorganic or organic base, at least one of Z and Z' representing a hydrogen atom; $R_1$ denotes a hydrogen atom, an optionally branched alkyl radical containing 2 to 18 carbon atoms, an alkenyl radical containing 3 to 18 carbon atoms, a radical $-(CH_2CH_2O)_nH$,

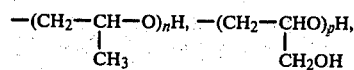

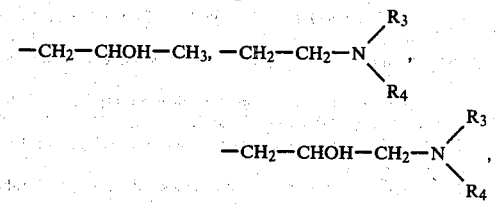

$-(CH_2)_mCO_2R$, in which R denotes H or an alkyl radical containing 1 to 8 carbon atoms, or $-(CH_2)_3-SO_3H$, or a salt of this acid with an organic or inorganic base, or also a divalent radical $-(CH_2)_m-$ or $-CH_2-CHOH-CH_2-$, m having the values 1 to 10, n having the values 1 to 20 and p having the values 1 to 6, and $R_3$ and $R_4$ each representing a hydrogen atom or an optionally branched or hydroxylic, alkyl radical, or together forming an amino-aliphatic heterocyclic ring with the nitrogen atom to which they are attached; $R_2$ denotes a hydrogen atom, an alkoxy radical containing 1 to 4 carbon atoms or a divalent radical $-O-$ bonded to the radical $R_1$ if the latter is also divalent; and q denotes 1 or 2, it being understood that, if q has the value 2, $R_1$ is a divalent radical forming a bridge between two 3-oxybenzylidene-bornan-2-one radicals, with the proviso that if $R_1$ denotes hydrogen, $R_2$ also denotes a hydrogen atom, as sun filters, and also the compounds as defined with the additional proviso that when q is 1 at least one of Z, Z', $R_1$ and $R_2$ is not hydrogen and when Z and Z' are both hydrogen $R_1$ is not $-CH_2-$ when $R_2$ is is $-O-$ as novel compounds.

Amongst the compounds of the invention, the compounds in Table 1 below may be mentioned in particular, in which Table the number of each compound is the same as that of its preparation example.

TABLE (1)

| No. |
|---|
| 1. 3-(3',4'-Methylenedioxybenzylidene)-bornan-2-one |
| 2. 3-(p-Hydroxybenzylidene)-bornan-2-one |
| 3. 3-(3',4'-Dimethoxybenzylidene)-bornan-2-one |
| 4. 3-[4'-(2-Hydroxy-3-morpholinopropoxy)-benzylidene]-bornan-2-one |
| 5. 3-[4'-(2-Hydroxy-3-piperidinopropoxy)-benzylidene]-bornan-2-one |

TABLE (1)-continued

No.
6. 3-[4'-(β-Hydroxyethoxy)-benzylidene]-bornan-2-one
7. 3-[4'-(2,3-Dihydroxypropoxy)-benzylidene]-bornan-2-one
8. 3-(4'-Allyloxybenzylidene)-bornan-2-one
9. p,p'-(Butane-1,4-diyldioxy)-bis-(3-benzylidene-bornan-2-one)
10. 4-(2-Oxobornylidene-3-methyl)-phenoxyacetic acid
11. 4,5-Dimethoxy-2-(2-oxobornylidene-3-methyl)-benzenesulphonic acid
12. 3-(4'-Butoxy-3'-methoxybenzylidene)-2-oxobornane-10-sulphonic acid
13. 3-[4'-(ω-Carboxydecyloxy)-benzylidene]-2-oxobornane-10-sulphonic acid
14. 3-[4'-(2,3-Dihydroxypropoxy)-benzylidene]-2-oxobornane-10-sulphonic acid
15. Sodium 2-dodecyloxy-5-(2-oxobornylidene-3-methyl)-benzenesulphonate
16. 3-(4'-Dodecyloxybenzylidene)-bornan-2-one
17. 3-(4'-Dodecyloxybenzylidene)-2-oxobornane-10-sulphonic acid
18. 3-(4'-Butoxybenzylidene)-bornan-2-one
19. 3-(4'-Butoxybenzylidene)-2-oxobornane-10-sulphonic acid
20. Sodium 2-butoxy-5-(2-oxobornylidene-3-methyl)-benzenesulphonate
21. 3-(4'-Hexadecyloxybenzylidene)-bornan-2-one
22. 3-(4'-Hexadecyloxybenzylidene)-2-oxobornane-10-sulphonic acid
23. 3-(4'-Carboxymethoxybenzylidene)-2-oxobornane-10-sulphonic acid
24. Sodium 3-(4'-carboxymethoxybenzylidene)-2-oxobornane-10-sulphonate
25. 3-[4'-(2-Hydroxy-3-morpholinopropoxy)-benzylidene]-2-oxobornane-10-sulphonic acid
26. 3-(3',4'-Methylenedioxybenzylidene)-2-oxobornane-10-sulphonic acid
27. 3-(3',4'-Dimethoxybenzylidene)-2-oxobornane-10-sulphonic acid
28. 3-(4'-Octyloxybenzylidene)-bornan-2-one
29. 3-(4'-Octyloxybenzylidene)-2-oxobornane-10-sulphonic acid
30. Sodium 3-[4-(2-oxobornylidene-3-methyl)-phenoxy]-propanesulphonate
31. Sodium 3-(4'-butoxybenzylidene)-2-oxobornane-10-sulphonate
32. Sodium 3-[4'-(2,3-dihydroxypropoxy)-benzylidene]-2-oxobornane-10-sulphonate
33. Sodium 3-(3',4'-dimethoxybenzylidene)-2-oxobornane-10-sulphonate
34. Sodium 3-(3',4'-methylenedioxybenzylidene)-2-oxobornane-10-sulphonate
35. Sodium 3-[4'-(2-hydroxy-3-morpholinopropoxy)-benzylidene]-2-oxobornane-10-sulphonate
36. Sodium 3-(4'-dodecyloxybenzylidene)-2-oxobornane-10-sulphonate

TABLE (1)-continued

No.
37. Sodium 3-(4'-hexadecyloxybenzylidene)-2-oxobornane-10-sulphonate
38. Sodium 3-(4'-butoxy-3'-methoxybenzylidene)-2-oxobornane-10-sulphonate The value of the compounds of the present invention can be demonstrated by comparing the spectra for the transmission of ultraviolet light through decimolar solutions (0.1 mol per liter), on the one hand of the compounds of the invention and on the other hand of the compounds of the prior art. In general, it is found that the compounds of formula I strongly absorb ultraviolet radiation over a broad range including wavelengths of from 290 to 340 nanometers, in particular from 315 to 340 nm. The following Table (2) indicates the transmitted flux, as a percentage relative to the incident flux, for wavelengths varying from 290 to 375 nm in 5 nm intervals. The compounds representing the prior art are:

A. benzylidene-camphor
B. 2-methyl-5-(2-oxobornylidene-3-methyl)-benzenesulphonic acid;
C. 4-(2-oxobornylidene-3-methyl)-phenyltrimethylammonium methylsulphate; and
D. 2,4-dihydroxybenzophenone, having a broad spectrum but a low absorption.

The compounds according to the invention are represented by numbers 18, 16, 20 and 3.

Moreover, those compounds, according to the invention, of which the formula contains a substituent $Z=SO_3H$ possess a completely remarkable property. In fact, in the anhydrous form or in a minimum state of hydration which is less than or equal to 0.5 $H_2O$, they are strongly coloured, as are their solutions in organic solvents, their colour varying from yellow to orange-red. On the other hand, in aqueous solution or in the form of salts, or also in the hydrated crystalline form obtained by equilibration with the atmosphere during drying in air, these compounds are colourless.

Only the benzylidene-bornanonesulphonic acids containing the "oxy" radical in the para-position possess this property, which has not been observed with any compound of the prior art.

Moreover, the anhydrous and the hydrated forms posess substantially different melting points, as indicated in Table (3) below.

TABLE (2)

| Wavelength region (nm) | Percentage of transmitted flux relative to the incident flux* | | | | | | | |
|---|---|---|---|---|---|---|---|---|
| | A | B | C | D | Compound 18 | Compound 16 | Compound 20 | Compound 3 |
| 290–295 | 1 | 0.5 | 1 | 4 | 3.5 | 3.5 | 3.5 | 6 |
| 295–300 | 1 | 0.5 | 2 | 6 | 2 | 2 | 2 | 4 |
| 300–305 | 2 | 0.5 | 5 | 7 | 1 | 1 | 1 | 4 |
| 305–310 | 4 | 1 | 17 | 9 | 0.5 | 0.5 | 0.5 | 3 |
| 310–315 | 12 | 2 | 53 | 9 | 0.3 | 0.3 | 0.5 | 2 |
| 315–320 | 33 | 4.5 | 82 | 9 | 0.3 | 0.3 | 0.5 | 1 |
| 320–325 | 63 | 14 | 89 | 9 | 0.3 | 0.3 | 0.5 | 1 |
| 325–330 | 81 | 38 | 91 | 9.5 | 0.5 | 0.5 | 1 | 1 |
| 330–335 | 85 | 65 | 91 | 11 | 1 | 1 | 2 | 1 |
| 335–340 | 88 | 81 | 91 | 14 | 3 | 2 | 4 | 2 |
| 340–345 | 89 | 88 | 91 | 19 | 8 | 7 | 11 | 3 |
| 345–350 | 89.5 | 92 | 91 | 28 | 19 | 16 | 21 | 6 |
| 350–355 | 90 | 93 | 91 | 39 | 35 | 34 | 37 | 12 |
| 355–360 | 91 | 94 | 91 | 52 | 60 | 50 | 51 | 23 |
| 360–365 | 91 | 96 | 91 | 66 | 72 | 77 | 65 | 41 |
| 365–370 | 91 | 96 | 91 | 76 | 81 | 82 | 72 | 55 |

TABLE (2)-continued

| Wavelength region (nm) | Percentage of transmitted flux relative to the incident flux* | | | | | | | |
|---|---|---|---|---|---|---|---|---|
| | A | B | C | D | Compound 18 | Compound 16 | Compound 20 | Compound 3 |
| 370–375 | 91 | 96 | 91 | 86 | 87 | 86 | 79 | 68 |

*Measurement was carried out under the same conditions for each compound through a ten micron thick decimolar solution.

TABLE (3)

| Compound No. | Colour | Anhydrous form* Melting point in °C. | Hydrated form** Melting point | State of hydration | |
|---|---|---|---|---|---|
| 26 | Bright yellow | 225° | *** | 2.5 | $H_2O$ |
| 27 | Orange | 210° | *** | 2 | $H_2O$ |
| 19 | Bright yellow | 188° | 140° | 2 | $H_2O$ |
| 17 | Yellow | 140° | 105° | 1.5 | $H_2O$ |
| 23 | " | 205° | 96° | 3 | $H_2O$ |
| 12 | Bright yellow | 140° | 120° | 1.5 | $H_2O$ |
| 13 | " | 160° | 120° | 1.5 | $H_2O$ |
| 22 | Green-yellow | 108° | 95° | 1.5 | $H_2O$ |

*Compounds nos. 19, 26 and 13 are not in the anhydrous form but in the minimum state of hydration of the isolated product, containing about 0.5 $H_2O$.
**Colourless.
***Indeterminable melting point. On heating, the product gradually loses water to give the coloured anhydrous form.

Similarly, compound 11, which contains a radical $Z'=SO_3H$ on the nucleus, melts at 204° C. if it is anhydrous (yellow powder) and at 107° C. if it is in equilibrium with air (white trihydrate).

This invention also provides a process for the preparation of the compounds of formula I.

The compounds of the general formula I in which $Z'$ denotes a hydrogen atom and $R_1$ is not hydrogen can be prepared as indicated below, either by method 1 or by method 2 (provided, in this case, that $R_2$ represents a hydrogen atom).

The compounds of the formula I in which $Z'=H$ and $R_1$ and $R_2$ both denote hydrogen can be prepared by the acid hydrolysis of a corresponding compound haaving an ether group $OR_1$ (preferably with $R_1=CH_3$), using, for example, pyridine hydrochloride.

Method of preparation 1

In general, the compounds of the formula I in which $Z'$ denotes a hydrogen atom, $R_1$ is not H and $q=1$ can be prepared by condensing an aromatic aldehyde of the formula II:

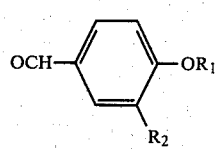

II in which $R_1$ and $R_2$ have the abovementioned meanings, with the product resulting from the reaction of bornan-2-one, or its derivative sulphonated in the 10-position, with, respectively, one or two equivalents of an alkali metal or of a strong base such as an alkali metal amide, hydride or alcoholate. The reaction can be carried out in the presence of an inert solvent such as benzene, toluene or ether. It leads to a compound of the formula III below:

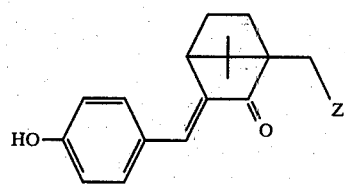

III in which Z, $R_1$ and $R_2$ are as defined in formula I and $q=1$, except that $R_1$ does not represent hydrogen. Moreover, some aldehydes of the formula II are new compounds which can be used either as synthesis intermediates or for their cosmetic properties.

Starting from the compounds of the formula III, the compounds of the formula I in which $R_1=R_2=H$ can be prepared by the acid hydrolysis of a corresponding compound having the ether group $—OR_1$, preferably the corresponding methyl ether in the presence of a hydrolysing agent, such as pyridine hydrochloride, and this makes it possible to obtain the compounds of the formula IV below:

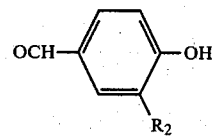

IV in which Z has the abovementioned meanings.

The compounds of formula I in which $q=2$ can be prepared in accordance with a process comprising 2 condensation stages. In the first stage, two molecules of a para-hydroxylic aldehyde of the formula VI:

VI in which $R_2$ denotes H or an alkoxy radical containing 1 to 4 carbon atoms, are condensed, in the presence of an inert solvent, with one molecule of a compound of the formula $X-R_1-X$ in which $R_1$ is an abovementioned divalent radical and X denotes a halogen, an alkanesulphonate or an arenesulphonate, to give a compound of the formula II Bis

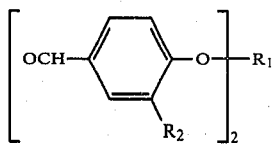

II Bis

In the second stage of the process, one molecule of the above-mentioned compound of formula II Bis is condensed, in the presence of an inert solvent, with two molecules of the product resulting from the reaction of bornan-2-one, or its derivative sulphonated in the 10-position, with, respectively, 2 or 4 equivalents of an alkali metal or of a strong base such as an alkali metal amide, hydride or alcoholate, to give the corresponding compound of the formula I in which $q=2$.

Method of preparation 2

This method uses a 3-benzylidene-bornan-2-one of the formula IV' below, as the starting product, to give a compound of the general formula I in which $q=1$, either by means of a substitution reaction or by means of an addition reaction.

Variant 2(a) using a substitution reaction

A 3-benzylidene-bornan-2-one of the formula IV', which has a hydroxyl radical in the para-position of the benzylidene and in which Z has the abovementioned meaning and $R_2$ denotes H or alkoxy, is reacted with a compound of the formula $R_1X$ in which X denotes a halide, an alkylsulphate, an alkanesulphonate or an arenesulphonate and $R_1$ denotes an alkyl, alkenyl or hydroxyalkyl radical as defined for formula I, in accordance with the equation:

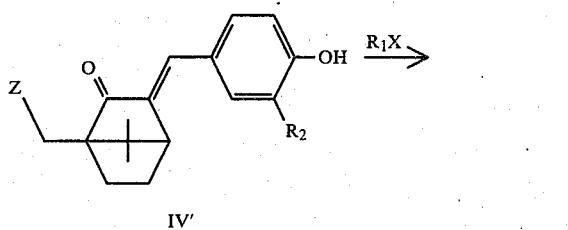

IV'

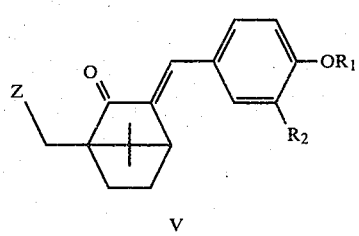

V to give a compound of the formula V above, in which Z, $R_1$ and $R_2$ have the abovementioned meanings and $q=1$.

In order to obtain a compound of formula I in which $R_1$ denotes an abovementioned divalent radical and $q=2$, 2 molecules of a compound of the formula IV' are reacted with one molecule of a compound of the formula $X-R_1-X$ in which $R_1$ is an abovementioned divalent radical and X has the abovementioned meaning with the exception of alkyl-sulphate.

In accordance with the process of variant 2(a), it is also possible firstly to prepare an aldehyde of the formula II from an aldehyde of the formula VI:

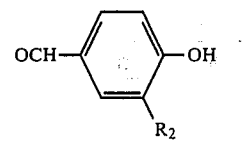

VI in which $R_2$ denotes H or alkoxy containing 1 to 4 carbon atoms, with which latter aldehyde the compound $R_1X$, as defined above, is reacted. The substitution product thus obtained can then be condensed, as in method 1, with bornan-2-one, or its derivative sulphonated in the 10-position, to give a compound of the formula III.

Variant 2(b) using the addition reaction.

A compound of the formula IV', in which Z and $R_2$ have the abovementioned meanings, is reacted with a reactive heterocyclic compound of the formula BY, in which $Y=-O-$, $-NR_3-$, $-N^+R_3R_4-$ or $-SO_2-O-$ and B denotes a heterocyclic radical producing the radical $BYH=R_1$ after the ring-opening and addition reaction, in accordance with the equation:

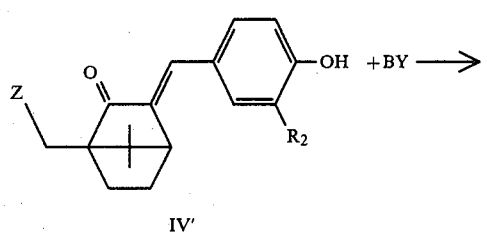

IV'

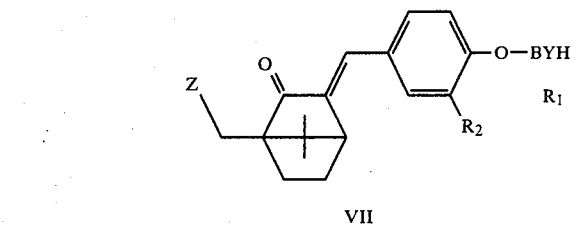

VII to give a compound of the formula VII in which $R_2$ denotes H or an alkoxy radical and Z and $R_1$ have the meanings defined for the formula I, except that $R_1$ does not represent hydrogen, alkyl, alkenyl or $(CH_2)_mCO_2R$ and does not denote a divalent radical.

Again in this case, in accordance with the process of variant 2(b), it is also possible to prepare an aldehyde of the formula II from an aldehyde of the formula VI in which $R_2$ denotes H or alkoxy, with which latter aldehyde a heterocyclic compound of the formula BY, as defined above, is reacted. The addition product thus obtained can then be condensed with bornan-2-one, or its derivative sulphonated in the 10-position, as indicated in method 1 above, to give the compound of the formula III in which $R_2$ has the meaning hydrogen or alkoxy and Z and $R_1$ have the meanings defined for the formula I, except that $R_1$ does not represent H, alkyl, alkenyl, $-(CH_2)_mCO_2R$ or a divalent radical.

The reactive heterocyclic compound of the formula BY can be propanesultone, an oxirane, such as glycidol, ethylene oxide, propylene oxide or epichlorohydrin, or an azetidinium salt or an aziridine.

The process according to method 2, whether this be variant 2(a) or variant 2(b), is preferably carried out in the presence of a basic agent such as an alkali metal hydroxide or carbonate or alkaline earth metal hydroxide or carbonate, a metal or an alkali metal alcoholate or hydride; the reaction solvent can be water or an organic solvent such as an alcohol, dioxane, dimethylsulphoxide or dimethylformamide.

The compounds of formula I in which Z=H and Z'=SO$_3$H or a corresponding metal salt can be prepared by sulphonating a compound of the formula I, in which Z=Z'=H. The sulphonation can be carried out with, for example, concentrated sulphuric acid, oleum or chlorosulphonic acid, and the resulting acid is optionally salified with an organic or inorganic base.

This invention also provides a cosmetic composition containing, in an appropriate vehicle, one or more compounds of the formula I according to the invention, alone or in association with one or more other agents which absorb actinic radiation. In particular, they can be associated with agents which specifically filter the so-called UV-B radiation, the effect of which is to widen the zone of protection and thus to avoid the sensitisation of the skin surface to this particularly aggressive and reaction-provoking radiation. Amongst the agents which provide protection against UV-B radiation and which can be used together with the compounds of formula I, there may be mentioned salicylic acid esters, p-amino and p-dialkylaminobenzoic acid esters, benzylidene-camphor and its alkyl, ammonium, sulpho or substituted alkyl derivatives.

Suitable quaternary ammonium benzylidene-camphor derivatives include the compounds of the general formula:

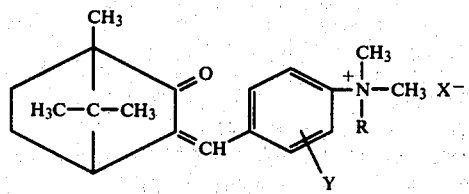

in which: R represents hydrogen or an alkyl group containing 1 to 12 carbon atoms, Y represents halogen, a methyl group or a hydrogen atom and X$^-$ represents a halide, an arylsulphonate, an alkylsulphonate, a camphosulphonate or an alkyl-sulphate, which compounds are described in French Patent No. 2,199,971, may be mentioned very particularly. The trimethylammonium-benzylidene-camphor salts may be especially mentioned.

Amongst the benzylidene-camphor compounds carrying a sulphonic acid radical, the compounds of the general formula:

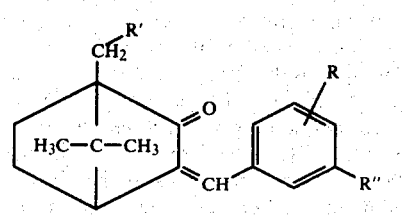

in which R denotes a hydrogen atom, a halogen atom, such as Cl or F, or an alkyl radical containing 1–4 carbon atoms and R' and R" each independently denote a hydrogen atom or a radical —SO$_3$M, in which M denotes H, an organic ammonium group or a metal, at least one of the radicals R' and R" not being H, which compounds are described in French Patent No. 2,282,426, may be mentioned very particularly. 5-(2-Oxobornylidene-3-methyl)-2-methylbenzene-sulphonic acid, 4-(2-oxobornylidene-3-methyl)-benzenesulphonic acid, 3-(p-methylbenzylidene)-2-oxobornane-10-sulphonic acid and 3-benzylidene-2-oxobornane-10-sulphonic acid and also their salts with inorganic or organic bases may be especially mentioned.

Amongst the alkyl-substituted benzylidene-camphor compounds, there may be mentioned, in particular, the compounds of the general formula:

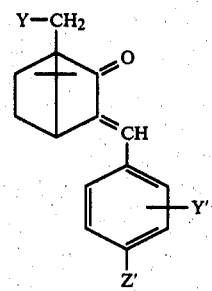

VIII in which Y and Y' denote H or SO$_3$H, and the corresponding salts with organic or inorganic bases, and Z' denotes the groups —CH$_2$Br, —CHBrBr, —CH$_2$I, —CH$_2$R, —CHR'R', —CHO or —COOR", in which R=—NR$_1$R$_2$, —N$^+$R$_1$R$_2$R$_3$, —OR$_4$, —OCOR$_5$, —SR$_6$, —CN, —COOR" or —SSO$_3$Na, R$_1$ and R$_2$ independently denote H, C$_{1-18}$ alkyl or hydroxyalkyl or together form, with the nitrogen atom, a heterocyclic ring such as morpholine, piperidine, pyrrolidine, piperazine, N-methylpiperazine or N-phenylpiperazine, R$_3$=C$_{1-4}$ lower alkyl, hydroxyalkyl or sulphonatopropyl, R$_4$=H, alkyl, polyoxyethylene, substituted or unsubstituted aryl, menthyl or dialkylaminoalkyl, R$_5$=alkyl, alkenyl, aryl or an aromatic or non-aromatic heterocyclic ring containing 5 to 6 ring members, R$_6$=H, alkyl, carboxyalkyl, aminoalkyl, hydroxyalkyl, aryl or 3-alanyl, R'=—OR'$_4$ or —SR'$_6$, in which R'$_4$ and R'$_6$ are as defined under R$_4$ and R$_6$, respectively, other than hydrogen, polyoxyethylene, hydroxyalkyl, 3-alanyl and aryl, and R"=hydrogen or alkyl, it being understood that if R=—NR$_1$R$_2$, the compound can be in the form of an addition salt with an inorganic or organic acid, and if R=N$^+$R$_1$R$_2$R$_3$, in which R$_1$ and R$_2$ are different from H, the ionic balance in the molecule is provided either by R$_3$, if the latter represents sulphonatopropyl, or by an anion X$^-$, where X is SO$_4$alkyl, SO$_3$aryl, SO$_3$alkyl or halogen.

The mono- and di-bromo compounds of the formula VIII can be obtained by selectively brominating the compounds of the formula:

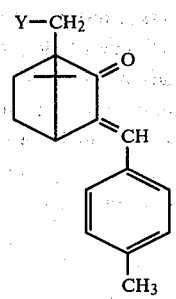

in which Y has the abovementioned meanings.

The bromination can be carried out either with bromine or with N-bromosuccinimide, in an inert solvent, such as a chlorohydrocarbon e.g. carbon tetrachloride, an ether, acetic acid, benzene or carbon disulphide, in the cold or with heat and with exposure to radiation in the wavelength range from 200 to 800 nm, optionally in the presence of a neutralising agent such as an alkali metal carbonate or alkaline earth metal carbonate.

In order to obtain the monobromo compound of the formula VIII (Z' denotes $—CH_2Br$) the reactants are used in a strictly stoichiometric amount, the yield being virtually quantitative. When the reaction is complete, the inorganic salts which may have formed can be filtered off, the solvents are driven off, the residual mixture is concentrated and, on cooling, a crude product is obtained which is recrystallised from a solvent, such as isopropanol, with a yield of 85 to 90%.

If the bromination is carried out with bromine, a solution of the latter in an inert solvent is typically introduced gradually, whilst stirring, into a solution of the compound of the formula VIII in the same inert solvent. If the bromination is carried out with N-bromosuccinimide, the two reactants can be introduced in total into the inert solvent at the start of the operation, and the reaction is carried out whilst stirring, preferably under the action of heat.

It is possible firstly to obtain the monobromo compound of the formula VIII, ($Z'=—CH_2Br$) and subsequently to prepare the dibromo compound of the formula VIII, in which $Z'=—CHBr_2$, from the monobromo compound, using either bromine or N-bromosuccinimide.

If it is desired to obtain a compound of the formula VIII in which Y denotes $SO_3H$, the reaction can be carried out in the absence of the neutralising agent or the reaction is terminated by acidification.

The compounds of the formula VIII can be prepared from the mono- and di-bromo derivatives described above.

In general, the compounds of the formula VIII in which Z' represents $—CH_2R$ can be prepared by reacting the monobromo compound with a nucleophilic compound containing the radical R.

The amino compounds of formula VIII i.e. R has the meaning $—NR_1R_2$ can be prepared by reacting the corresponding monobromo compound with an excess of ammonia or of the corresponding amine of the formula $HNR_1R_2$, in an inert solvent, preferably a chlorinated solvent, an aromatic solvent, an alcohol or also a dipolar aprotic solvent, such as dimethylformamide, optionally in the presence of a neutralising agent such as an alkali metal carbonate or alkaline earth metal carbonate.

The quaternary compounds of the formula VIII can be prepared by reacting the corresponding monobromo compound, under the action of heat, with a tertiary amine of the formula $NR_1R_2R_3$, in which the radicals $R_1$, $R_2$ and $R_3$ each have the abovementioned meanings, but not hydrogen. The reaction can be carried out in the absence of solvent or in the presence of a solvent such as those already mentioned above.

The compounds of the formula VIII in which R represents $—OR_4$, $—SR_6$ or $—OCOR_5$ can be prepared by reacting the corresponding monobromo compound with either an alcohol or a phenol of the formula $HOR_4$, or a thiol of the formula $HSR_6$, or an acid of the formula $HO-COR_5$, respectively, the radicals $R_4$, $R_5$ and $R_6$ having the abovementioned meanings. In general, the reaction is carried out in the presence of an inorganic base, for example an alkali metal hydroxide or carbonate or alkaline earth metal hydroxide or carbonate, an alkali metal alcoholate, sodium hydride or an alkali metal, or in the presence of an organic base such as triethylamine.

If $R_4$ represents hydrogen, the radical R then has the meaning $—OH$, and a generator of OH ions, which can be a carbonate or a hydroxide, is used as the reactant.

Similarly, if $R_6$ represents hydrogen, either an alkali metal hydrosulphide or thiourea can be used as the reactant, an alkaline hydrolysis then being carried out in accordance with the usual techniques for the preparation of thiols.

The compounds of the formula VIII in which Z' represents $—CHR'R'$, the radical R' representing $—OR'_4$ and the radical $R'_4$ having the abovementioned meanings, can be prepared by reacting the dibromo compound with an alcohol of the formula $HOR'_4$. The reaction is carried out in the presence of a base, as in the process for the preparation of the monosubstituted compounds containing the radicals $R_4$ and $R_6$.

The aldehydes corresponding to the general formula VIII ($Z'=—CHO$) can be prepared by hydrolysing, in an aqueous acid medium, an acetal of the general formula VIII in which R' represents $—OR'_4$.

Furthermore, the same aldehyde can be obtained by the direct oxidation of the monobromo derivative.

The compounds in which Z' represents $—CHR'R'$, R' representing $SR'_6$, are preferably prepared from the corresponding aldehyde ($Z'=—CHO$) and a thiol $R'_6SH$ (2 molar equivalents), with an acid catalyst, in accordance with the known methods for the preparation of mercaptals.

The acids of the general formula VIII in which $Z'=—COOH$ can be prepared by oxidising an aldehyde of the general formula VIII ($Z'=—CHO$).

The esters of the general formula VIII in which Z' represents $—COOR''$ can be obtained by esterifying the acid with an alcohol of the formula $HOR''$ in which R" has the abovementioned meanings.

The acids of the formula VIII ($Z'=—CH_2COOH$) can also be prepared by oxidising the corresponding nitriles, which can themselves be prepared by reacting the monobromo compound with a cyanide, and the corresponding esters can be obtained by esterification with an alcohol of the formula $HOR''$. Finally, the quaternary compounds of the general formula VIII can also be prepared by quaternising the compounds of the general formula VIII in which Z' represents $—CH_2—NR_1R_2$, in which compounds $R_1$ and $R_2$ do not represent hydrogen. Amongst the quaternising agents which can advantageously be used, there may be mentioned: dimethyl sulphate and diethyl sulphate, alkyl halides or sulphonates, hydroxyalkyl halides and propanesultone. Amongst the compounds of the formula VIII which can be used in the compositions of this invention, the following may be mentioned;

3-(4-Bromomethylbenzylidene)-camphor. M.p.=125° C.

3-(4-Dibromomethylbenzylidene)-camphor. M.p.=96° C.

3-(4-Bromomethylbenzylidene)-campho-10-sulphonic acid. M.p.=232° C.

3-(4-Dimethylaminomethylbenzylidene)-camphor. M.p.=65° C.

3-(4-Diethylaminomethylbenzylidene)-camphor (oil).

3-(4-Diethylaminomethylbenzylidene)-camphor hydrochloride. M.p.=245° C.

4-(2-Oxobornylidene-3-methyl)-benzyldiethylammonium camphosulphonate. M.p.=170° C.

3-[4-Bis-(2-hydroxyethyl)-aminomethylbenzylidene]-camphor (oil).

3-[4-Bis-(2-hydroxyethyl)-aminomethylbenzylidene]-camphor hydrochloride. M.p.=230° C.

3-(4-Diisopropylaminomethylbenzylidene)-camphor. M.p.=89° C.

3-(4-Diisopropylaminomethylbenzylidene)-camphor hydrochloride. M.p.=205° C.

3-(4-Dibutylaminomethylbenzylidene)-camphor (oil).

3-(4-Dibutylaminomethylbenzylidene)-camphor hydrochloride. M.p.=139° C.

3-[4-Bis-(octadecyl)-aminomethylbenzylidene]-camphor. M.p.=37° C.

3-(4-Piperidinomethylbenzylidene)-camphor. M.p.=96° C.

3-(4-Morpholinomethylbenzylidene)-camphor. M.p.=89° C.

4-[4-(2-Oxobornylidene-3-methyl)-benzylamino]-benzoic acid. M.p.=207° C.

4-(2-Oxobornylidene-3-methyl)-benzyldiethylmethylammonium p-toluenesulphonate. M.p.=155° C.

4-(2-Oxobornylidene-3-methyl)-benzyldiethylmethylammonium methanesulphonate. M.p.=162° C.

N-[4-(2-Oxobornylidene-3-methyl)-benzyl]-N-methylmorpholinium methanesulphonate. M.p.=192° C.

N-[4-(2-Oxobornylidene-3-methyl)-benzyl]-N-methylmorpholinium methylsulphate. M.p.=160° C.

N-[4-(2-Oxobornylidene-3-methyl)-benzyl]-N-methylmorpholinium iodide. M.p.=200° C.

N-[4-(2-Oxobornylidene-3-methyl)-benzyl]-N-methylpiperidinium p-toluenesulphonate. M.p.=167° C.

N-[4-(2-Oxobornylidene-3-methyl)-benzyl]-N-methylpiperidinium methanesulphonate. M.p.=170° C.

4-(2-Oxobornylidene-3-methyl)-benzyltriethylammonium bromide. M.p.=230° C.

4-(2-Oxobornylidene-3-methyl)-benzyl-tris-(2-hydroxyethyl)ammonium bromide (oil).

4-(2-Oxobornylidene-3-methyl)-benzyldimethyldodecylammonium bromide. M.p.=83° C.

4-(2-Oxobornylidene-3-methyl)-benzyldimethyltetradecylammonium bromide. M.p.=100° C.

3-(4-Hydroxymethylbenzylidene)-camphor. M.p.=35° C.

3-(4-Methoxymethylbenzylidene)-camphor. B.p.=175° C. under 0.25 mm Hg.

3-(4-Butoxymethylbenzylidene)-camphor. B.p.=210° C. under 0.5 mm Hg.

3-(4-Dodecyloxymethylbenzylidene)-camphor (pale yellow oil).

3-(4-Tetradecyloxymethylbenzylidene)-camphor. M.p.=35° C.

3-(4-Hexadecyloxymethylbenzylidene)-camphor. M.p.=40° C.

3-(4-Phenoxymethylbenzylidene)-camphor. M.p.=139° C.

3-[4-(α-Naphthoxymethyl)-benzylidene]-camphor. M.p.=120° C.

3-[4-(p-Benzoylphenoxymethyl)-benzylidene]-camphor. M.p.=122° C.

Methyl 2-[4-(2-oxobornylidene-3-methyl)-benzyloxy]-benzoate. M.p.=120° C.

2-[4-(2-Oxobornylidene-3-methyl)-benzyloxy]-benzoic acid. M.p.=128° C.

4-(2-Oxobornylidene-3-methyl)-benzyl tetradecanoate. M.p.=29° C.

4-(2-Oxobornylidene-3-methyl)-benzyl hexadecanoate. M.p.=30° C.

4-(2-Oxobornylidene-3-methyl)-benzyl benzoate. M.p.=63° C.

3-(4-Mercaptomethylbenzylidene)-camphor. M.p.=87° C.

3-(4-Methylthiomethylbenzylidene)-camphor. M.p.=44° C.

3-(4-Methylsulphinylmethylbenzylidene)-camphor. M.p.=119° C.

2-[4-(2-Oxobornylidene-3-methyl)-benzylthio]-acetic acid. M.p.=90° C.

2-[4-(2-Oxobornylidene-3-methyl)-benzylthio]-succinic acid. M.p.=210° C.

3-[4-(2-Oxobornylidene-3-methyl)-benzylthio]-alanine. M.p.=190° C.

3-[4-(β-Diethylaminoethylthiomethyl)-benzylidene]-camphor hydrobromide. M.p.=169° C.

3-[4-(Benzothiazol-2-ylthiomethyl)-benzylidene]-camphor. M.p.=114° C.

3-(4-Cyanomethylbenzylidene)-camphor. M.p.=127° C.

4-(2-Oxobornylidene-3-methyl)-phenylacetic acid. M.p.=134° C.

4-(2-Oxobornylidene-3-methyl)-benzoic acid. M.p.=240° C.

3-(4-Dimethoxymethylbenzylidene)-camphor. M.p.=98° C.

3-(4-Formylbenzylidene)-camphor. M.p.=116° C.

2-[4-(2-Oxobornylidene-3-methyl)-benzylthio]-benzoic acid. M.p.=198° C.

4-(2-Oxobornylidene-3-methyl)-benzyl 2,5-dihydroxybenzoate. M.p.=220° C.

4-(2-Oxobornylidene-3-methyl)-benzyl 3,5-di-(t-butyl)-4-hydroxybenzoate. M.p.=132° C.

4-(2-Oxobornylidene-3-methyl)-benzyl oleate.

3-[4-(2-Ethylhexyloxymethyl)-benzylidene]-camphor (oil).

3-(4-Octyloxymethylbenzylidene)-camphor. B.p.=240° C. under 0.1 mm Hg.

3-(4-Hexyloxymethylbenzylidene)-camphor.

3-(4-Menthyloxymethylbenzylidene)-camphor (oil).

3-[4-(2,6-Di-(t-butyl)-4-methylphenoxymethyl)-benzylidene]-camphor. M.p.=135° C.

3-(4-Dimethylaminoethoxymethylbenzylidene)-camphor hydrochloride. M.p.=152° C.

3-[4-(2-Oxobornylidene-3-methyl)-benzylthio]-propionic acid.

4-(2-Oxobornylidene-3-methyl)-benzyltrimethylammonium methylsulphate. M.p.=177° C.

N-[4-(2-Oxoborynylidene-3-methyl)-benzyl]-N-(2-hydroxyethyl)-morpholinium chloride. M.p.=200° C.

N-(2-Hydroxyethyl)-N-[4-(2-oxobornylidene-3-methyl)-benzyl]-dimethylammonium bromide. M.p.=210° C.

3-[4-(2-Oxobornylidene-3-methyl)-benzyldimethylammonio]-propanesulphonate. M.p.=260° C.

3-(4-Oleyloxymethylbenzylidene)-camphor (oil).

3-(4-Iodomethylbenzylidene)-camphor. M.p.=108° C.

3-[4-($\beta$-Hydroxyethoxymethyl)-benzylidene]-camphor. M.p.=54° C.

4-(2-Oxobornylidene-3-methyl)-benzyldithiodiacetic acid. M.p.=116° C.

3,3'-[4-(2-Oxobornylidene-3-methyl)-benzyldithio]-dipropionic acid.

$\alpha,\alpha'$-[4-(2-Oxobornylidene-3-methyl)-benzyldithio]-disuccinic acid.

3-[4-(7-Hydroxy-2,5-dioxaheptyl)-benzylidene]-camphor (oil). Bis-N,N'-[4-(2-Oxobornylidene-3-methyl)-benzyl]-piperazine. M.p.=204° C.

N-Methyl-N-[4-(2-oxoborylidene-3-methyl)-benzyl]-piperazinium bromide. M.p.=200° C.

N-Methyl-N,N'-bis-[4-(2-oxobornylidene-3-methyl)-benzyl]-piperazinium bromide. M.p.=200° C. (with decomposition).

N,N'-Bis-(2-hydroxyethyl)-N,N'-bis[4-(2-oxobornylidene-3-methyl)-benzyl]-piperazinium dibromide.

N,N'-Bis-(2-hydroxypropyl)-N,N'-bis-[4-(2-oxobornylidene-3-methyl)-benzyl]-piperazinium dibromide.

N,N'-Bis-(2-hydroxyethyl)-N-[4-(2-oxobornylidene-3-methyl)-benzyl]-piperazinium bromide. M.p.=184° C.

Amongst the compounds derived from benzylidenecamphor, the esters derived from compound No. 2 in Table I may also be mentioned, in particular: 3-(4'-acetyloxybenzylidene)-bornan-2-one, 3-[4'-(but-2-enoyloxy)-benzylidene]-bornan-2-one, 3-(4'-hexanoyloxybenzylidene)-bornan-2-one, 3-(4'-tetradecanoyloxybenzylidene)-bornan-2-one, 3-[4'-(isobut-2-enoyloxy)-benzylidene]-bornan-2-one, 3-(4'-propenoyloxybenzylidene)-bornan-2-one and 3-(4'-hexadecamoyloxybenzylidene)-bornan-2-one.

The composition of the present invention can be in the form of, for example, solutions, aqueous-alcoholic or oily-alcoholic lotions, oil-in-water or water-in-oil emulsions (creams and milks), or gels, and in general, in all the forms used for anti-actinic compositions. They can contain, in particular, thickeners, superfatting agents, softeners, moisturisers, emollients, wetting agents and surface-active agents, and also preservatives, anti-foam agents and perfumes. The compositions of this invention can also contain one or more propellants such as Freons (fluorinated hydrocarbons), carbon dioxide gas, nitrous oxide or volatile hydrocarbons, and can be presented in the form of a spray or aerosol.

The compositions of the invention generally contain from 0.5 to 10%, preferably from 1 to 6%, by weight, of one or more compounds of formula I. The solvents or suspending agents used are typically water, a monohydric or polyhydric alcohol containing 1 to 18 carbon atoms, or a mixture thereof, or an aqueous-alcoholic solution. The alcohols used are preferably ethanol, isopropyl alcohol, glycerol, propylene glycol, sorbitol, oleyl alcohol or hexylene glycol; the aqueous-alcoholic mixtures are preferably water/ethanol mixtures.

The compositions of this invention can be colourless or coloured, for example with pigments or dyestuffs which are usually employed in anti-sunburn compositions, in particular iron oxides or titanium oxides, in an amount of, say 0.001 to 0.2% by weight, relative to the total weight of the composition.

They can also contain agents which assist the hydration or slow down the dehydration of the skin, such as salts of pyrrolidonecarboxylic acid, salts of hydroxyacids, aminoacids and urea.

If the compound is a sulphonic acid of the formula I in which Z or Z' denotes $SO_3H$, it is preferably totally or partially neutralised with an inorganic or organic base; amongst these bases, there may be mentioned sodium hydroxide, potassium hydroxide, magnesium carbonate, alkanolamines, arginine and lysine.

Similarly, the compounds of the formula I in which the main group is basic, such as the amines, can be partially or totally neutralised with an inorganic or organic acid, depending on the desired solubility or the desired pH.

Amongst the cosmetic adjuvants which can be included in the compositions, generally at a concentration of 1 to 98% by weight, relative to the total weight of the composition, there may be mentioned lanoline, triglycerides of fatty acids, essential oils, polyethylene glycols, oxyethyleneated lanolines, isopropyl palmitate and myristate, cetyl/stearyl, cetyl and stearyl alcohols, glyceryl monostearate and distearate, polyethylene glycol monostearates and distearates, branched esters of fatty acids, inorganic and organic waxes and oils and anionic or non-ionic surface-active agents.

The following Examples further illustrate the present invention; unless otherwise stated, the percentages are parts by weight and the temperatures are degrees centigrade.

The compositions of the invention are illustrated in the following manner: milks by Examples $A_1$ to $A_4$, creams by Examples $B_1$ to $B_6$, lotions by Examples $C_1$ and $C_2$, foams by Example $D_1$, sprays by Example $E_1$ and sun oils by Examples $F_1$ to $F_3$.

PREPARATION EXAMPLES

PREPARATION PROCESSES ACCORDING TO METHOD 1

EXAMPLE 18

Preparation of compound no. 18 in Table (1)
3-(4'-Butoxybenzylidene)-bornan-2-one A solution of 100 millimols (15.2 g) of camphor in 250 ml of toluene is heated for 1 hour at the boil with 100 mmols (5.4 g) of sodium methylate. After cooling, 100 mmols (17.8 g) of p-butoxybenzaldehyde are introduced and the mixture is heated at the reflux temperature for 4 hours. The reaction mixture is cooled and 50 ml of water are then added; the toluene phase is separated off, washed with water, dried over sodium sulphate and concentrated to dryness. The solid residue is crystallised from aqueous isopropanol. After drying, 12 g of a white powder, which melts at 62°, are collected.

Analysis: $C_{21}H_{28}O_2$; Calculated % C 80.77, H 8.97; Found % 80.75, 8.79.

Compounds nos. 1, 3, 4, 16, 21 and 28 in Table (1) are obtained in the same manner, as indicated in Table (4) below, the p-butoxybenzaldehyde being replaced by the aldehydes indicated:

TABLE (4)

| Compound no. | Benzaldehyde used carrying the radicals | Appearance | Melting point | Analysis C Calculated % | Found % | H Calculated % | Found % |
|---|---|---|---|---|---|---|---|
| 16 | p-dodecyloxy | white needles | 60° | 82.08 | 82.28 | 10.38 | 10.51 |
| 21 | p-hexadecyloxy | whitish solid | 69° | 82.50 | 81.80 | 10.83 | 10.63 |
| 4 | p-(2-hydroxy-3-morpholinopropoxy) | whitish solid | 130° | 72.18 | 71.93 | 8.27 | 8.24 |
| 3 | 3,4-dimethoxy | white powder | 73° | 76.00 | 76.00 | 8.00 | 7.99 |
| 1 | 3,4-methylenedioxy | white needles | * | 76.06 | 76.15 | 7.04 | 7.13 |
| 28 | 4-octyloxy | white needles | 58–59° | | | | |

* compound prepared from d,l-camphor: m.p. = 135°
compound prepared from d-camphor: m.p. = 162°

EXAMPLE 26

Preparation of compound no. 26 in Table (1)
3-(3′,4′-Methylenedioxybenzylidene)-2-oxobornane-10-sulphonic acid A mixture of 69.6 g of campho-10-sulphonic acid and 32.4 g of sodium methylate in 1,200 ml of toluene is heated at the reflux temperature for 15 minutes, whilst stirring. 42 g of piperonal in a small amount of toluene are added and heating is continued for 4 hours under reflux. After cooling, 600 ml of water are poured into the reaction mixture. The precipitate formed is filtered off, washed with water and dried over phosphorus pentoxide. 93 g of the sodium salt of compound 26 are thus collected in the form of a white powder which melts at 220°.

The resulting sodium salt is dissolved in water at the boil; excess concentrated hydrochloric acid is then added to the solution. A yellowish oil precipitates and gradually solidifies. After filtration and draining, the product is dried over potassium hydroxide. A yellow solid, which melts at 225°, is obtained.

Analysis: $C_{18}H_{20}O_6S$; Calculated % C 59.34, H 5.49, S 8.79; Found % 59.09, 5.50, 8.80.

Compounds nos. 12, 14, 17, 19, 22, 25, 26, 27, 29, 31, 32, 33, 34, 35, 36, 37 and 38 in Table (1) are prepared in the same manner, as indicated in Table (5) below.

TABLE (5)

| Compound no. | Z | Benzaldehyde used, carrying the radicals | Melting point | State of hydration | Analysis C calculated % found % | H calculated % found % | S calculated % found % |
|---|---|---|---|---|---|---|---|
| 19 | SO₃H | p-butoxy | 188° | 0.5 H₂O | 62.84 / 63.14 | 7.14 / 7.15 | 7.98 / 7.72 |
| 31 | SO₃Na | p-butoxy | 180° | | | | |
| 25 | SO₃H | p-(2-hydroxy-3-morpholinopropoxy) | 340° (dec.) | 2 H₂O | 55.92 / 55.97 | 7.18 / 6.95 | 6.22 / 6.37 |
| 35 | SO₃Na | p-(2-hydroxy-3-morpholinopropoxy) | 160° | 2 H₂O | | | |
| 14 | SO₃H | p-(2,3-dihydroxypropoxy) | 95° | 1.5 H₂O | 54.91 / 54.55 | 6.64 / 6.51 | 7.32 / 7.60 |
| 32 | SO₃Na | p-(2,3-dihydroxypropoxy) | 160° | 3 H₂O | 49.38 / 49.44 | 6.38 / 6.10 | 6.58 / 6.64 |
| 27 | SO₃H | 3,4-dimethoxy | 210° | | 60.00 / 59.91 | 6.32 / 6.27 | 8.43 / 8.43 |
| 33 | SO₃Na | 3,4-dimethoxy | 240° | | | | |
| 26 | SO₃H | 3,4-methylenedioxy | 225° | 0.5 H₂O | 57.91 / 57.84 | 5.63 / 5.50 | 8.60 / 8.60 |
| 29 | SO₃H | 4-octyloxy | 153° | | | | |
| 34 | SO₃Na | 3,4-methylenedioxy | 220° | | | | |
| 17 | SO₃H | p-dodecyloxy | 140° (dec.) | | 69.05 / 68.88 | 8.73 / 8.94 | 6.35 / 6.40 |
| 36 | SO₃Na | p-dodecyloxy | 135° | | | | |
| 22 | SO₃H | p-hexadecyloxy | 108° | | 70.71 / 70.57 | 9.29 / 9.12 | 5.71 / 5.78 |
| 37 | SO₃Na | p-hexadecyloxy | 125° | 3 H₂O | 62.26 / 62.55 | 8.96 / 8.80 | 5.03 / 4.85 |
| 12 | SO₃H | 4′-butoxy-3′-methoxy | 120° | 1.5 H₂O | 58.80 / 58.97 | 7.35 / 7.17 | 7.13 / 7.30 |
| 38 | SO₃Na | 4′-butoxy-3′-methoxy | 150° | | | | |

EXAMPLE 23

Preparation of compound no. 23 in Table (1)
3-(4′-Carboxymethoxybenzylidene)-2-oxobornane-10-sulphonic acid A mixture of 63 g of campho-10-sulphonic acid and 32 g of sodium methylate in 500 ml of toluene is heated for 30 minutes under reflux. A solution of 63 g of butyl p-formylphenoxyacetate in toluene is then introduced. The resulting reaction mixture is heated for 2 hours at the reflux temperature. After cooling, 250 ml of water are added; the aqueous phase is separated off and acidified to pH 4 with hydrochloric acid; the precipitate formed is filtered off and washed with cold water. After drying, 63 g of a whitish solid, which melts at about 265° and corresponds to the sodium sulphonate (compound no. 24), are thus obtained.

| Acid number calculated | 2.40 | milliequivalents/g |
|---|---|---|
| found | 2.43 | " |

41.6 g of compound no. 24 are triturated with 250 ml of 6 N hydrochloric acid. The mixture is heated at 60° for a few minutes. The precipitate which appears on cooling is filtered off, washed with a small amount of ice-cooled water and drained. After drying in air, 33 g of a white solid, which melts at 96° and corresponds to compound no. 23 in the form of the trihydrate, are obtained.

Analysis: C 50.89, H 6.25, S 7.14, 50.56, 6.16, 7.35.

Compound no. 13 is prepared in the same manner and is obtained, after drying in air, in the form of a yellowish powder which melts at 140° and corresponds to the hemihydrate.

Analysis: $C_{28}H_{40}SO_7.\frac{1}{2} H_2O$; Calculated % C 63.52, H 7.75, S 6.05; Found % 63.26, 7.64, 6.26.

EXAMPLE 11

Preparation of compound no. 11 in Table (1)
4,5-Dimethoxy-2-(2-oxobornylidene-3-methyl)-benzenesulphonic acid A solution of 45 g of 3-(3',4'-dimethoxybenzylidene)-bornan-2-one (compound no. 3) in 200 ml of concentrated sulphuric acid is prepared. 200 ml of 20% strength oleum are added gradually to this solution, whilst stirring thoroughly. The temperature is kept below 5° for a further 2 hours after the addition is complete. The reaction mixture is then poured onto crushed ice; the precipitate is washed with 6 N hydrochloric acid, drained and dried in air. 43 g of a whitish powder, which melts at 107° and corresponds to compound no. 11 in the form of the trihydrate, are obtained.

Analysis: $C_{19}H_{24}SO_6.3H_2O$; Calculated % C 52.53, H 6.91, S 7.37; Found % 52.75, 6.75, 7.57.

EXAMPLE 20

Preparation of compound no. 20 in Table (1) Sodium 2-butoxy-5-(2-oxobornylidene-3-methyl)-benzenesulphonate 25 g of 3-(p-butoxybenzylidene)-bornan-2-one (compound no. 18) are added in portions, at 5°, to 120 ml of concentrated sulphuric acid. The reaction mixture is stirred for several hours at ambient temperature; it is then poured into 250 ml of 6 N hydrochloric acid; the paste obtained is separated off by decantation and neutralised to pH 7 with aqueous sodium hydroxide solution. The solution is concentrated in dryness; the residue is taken up in hot isopropanol, the mixture is filtered and the alcoholic filtrate is evaporated to dryness. 25 g of a whitish solid, which melts at about 205° and of which the analysis corresponds to the monohydrate of compound no. 20, are obtained.

Analysis: $C_{21}H_{27}SO_5Na.H_2O$; Calculated % C 58.33, H 6.71, S 7.49; Found % C 58.15, H 6.77, S 7.73.

Compound no. 15 is prepared in the same manner from 3-(p-dodecyloxybenzylidene)-bornan-2-one (compound no. 16). It melts at about 270°.

EXAMPLE 2

Preparation of compound no. 2 in Table (1)
3-(p-Hydroxybenzylidene)-bornan-2-one A mixture of 172 g of 3-(p-methoxybenylidene)-bornan-2-one and 344 g of dry pyridine hydrochloride is heated under gentle reflux for 2 hours. After cooling, the reaction mixture is poured into 1 liter of water; the resulting solid precipitate, which is beige in colour, is filtered off, washed copiously with water and drained; it is then crystallised from 700 ml of isopropanol. 136 g of compound no. 2, which melts at 220°, are thus collected.

Analysis: $C_{17}H_{20}O_2$; Calculated % C 79.69, H 7.81; Found % 79.56, 7.96.

PREPARATION PROCESSES ACCORDING TO METHOD 2

EXAMPLE 5

Preparation of compound no. 5 in Table (1)
3-[4'-(2-Hydroxy-3-piperidinopropoxy)-benzyl]-bornan-2-one A solution 5.12 g of 3-(p-hydroxybenzylidene)-bornan-2-one (compound no. 2) in 25 ml of normal sodium hydroxide solution is added, in the course of 30 minutes, to an aqueous solution of 7.1 g of 2-hydroxy-4-azoniaspiro[3,5]nonane. The mixture is heated for 10 hours at 95° C. After cooling, it is extracted with ethyl ether and the ether extracts are dried over sodium sulphate and concentrated to dryness; the residue is crystallised from isopropyl ether to yield, after drying, 5.6 g of whitish crystals which melt at 106°.

Analysis: $C_{25}H_{35}NO_3$; Calculated % C 75.53, H 8.87, N 3.52; Found % 75.60, 8.97, 3.50.

Compound no. 4 is prepared under the same conditions from 3-(p-hydroxybenzylidene)-bornan-2-one and 3'-hydroxy-4-morpholine-1'-spiro-azetidinium; it is in the form of whitish crystals which melt at 130° and the identity of which was confirmed using the compound obtained in accordance with method 1 (Table 1).

EXAMPLE 30

Preparation of compound no. 30 in Table (1)
Sodium-3-[4-(2-oxobornylidene-3-methyl)-phenoxy]-propanesulphonate A mixture of 51 g of 3-(p-hydroxybenzylidene)-bornan-2-one (compound 2), 11.4 g of sodium methylate and 24.4 g of propanesultone in 400 ml of methanol is heated under reflux for 3 hours. The reaction mixture is concentrated to dryness. 78 g of a whitish powder, which starts to soften at about 150° but does not have a sharp melting point below 250°, are thus collected.

Analysis: $C_{20}H_{25}O_5SNa.1.5H_2O$; Calculated % C 56.20, H 6.56, S 7.49; Found % 56.01, 6.33, 7.80.

EXAMPLE 6

Preparation of compound no. 6 in Table (1)
3-[4'-(β-Hydroxyethoxy)-benzylidene]-bornan-2-one A mixture of 64 g (0.25 mol) of compound no. 2 and 21 g of β-chloroethanol in dimethylformamide (500 ml) is heated for 2 hours at 100°, in the presence of a basic agent, that is to say 26.5 g of sodium carbonate. After cooling, the inorganic salts are filtered off and the filtrate is concentrated to dryness. The residue is taken up in toluene and the mixture is washed with 5 N sodium hydroxide solution and then with water. The toluene phase is dried over sodium sulphate and concentrated to dryness. The residual syrup (37 g) crystallises slowly to give a whitish solid which melts at 68°.

Analysis: $C_{19}H_{24}O_3$; Calculated % C 76.00, H 8.00; Found % 65.88, 7.98.

Compounds 7, 8, 9 and 10 in Table (1) are obtained in accordance with an analogous procedure, as indicated in Table (6) below, which table shows the particular conditions of preparation and the reagent $R_1X$ employed for carrying out the substitution of compound no. 2.

TABLE (6)

| Compound no. | $R_1X$ | Conditions of preparation |  |  | Melting point | Analysis |  |  |  |
|---|---|---|---|---|---|---|---|---|---|
| | | | | | | C |  | H |  |
| | | Base used | solvent | heating | | calculated % | found % | calculated % | found % |
| 8 | $CH_2=CH-CH_2Br$ | $CO_3Na_2$ | DMF* | 1 hour 30 minutes/ 100° | 34° | 81.08 | 81.10 | 8.11 | 7.90 |
| 10 | $ClCH_2CO_2H$ | NaOH | $H_2O$ | 10 hours | 195° | 72.61 | 72.62 | 7.01 | 7.11 |
| 7 | $ClCH_2-\underset{\underset{OH}{\mid}}{CH}-CH_2OH$ | $CO_3K_2$ | DMF | 6 hours/ 140° | oil | 72.72 | 72.68 | 7.88 | 7.96 |
| 9 | $Br(CH_2)_4Br$ | $CO_3K_2$ | DMF | 4 hours/ 110° | 186° | 80.57 | 60.82 | 8.13 | 7.99 |

*DMF = dimethylformamide.

COMPOSITION EXAMPLES

A. COMPOSITIONS OF ANTI-SUNBURN MILKS:

EXAMPLE A₁: The following non-ionic protective milk is prepared:

| Sipol wax | 5 % |
|---|---|
| Vaseline oil | 6 % |
| Isopropyl myristate | 3 % |
| Dimethylpolysiloxane | 1 % |
| Cetyl alcohol | 1 % |
| Preservative | 0.3 % |
| Glycerol | 20 % |
| Compound no. 8 | 2 % |
| Benzylidene-camphor | 3 % |
| Perfume | 0.5 % |
| Water q.s.p. | 100 g % |

EXAMPLE A₂: The following protective milk is prepared:

| Oxyethyleneated cetyl/stearyl alcohol containing 25 mols of ethylene oxide (per mol of alcohol) | 5 % |
|---|---|
| Cetyl alcohol | 1 % |
| 2-Octyldodecanol | 15 % |
| Codex vaseline oil | 5 % |
| Unsaponifiable matter from lucerne | 0.2 % |
| Compound 20 | 1.5 % |
| 2-Ethylhexyl p-dimethylaminobenzoate | 2.5 % |
| Preservative | 0.2 % |
| Perfume | 0.5 % |
| Water q.s.p. | 100 g % |

EXAMPLE A₃: The following anti-sunburn milk is prepared:

| Sipol wax | 5 |
|---|---|
| Vaseline oil | 6 % |
| Isopropyl palmitate | 3 % |
| Silicone oil | 1 % |
| Cetyl alcohol | 1 % |
| Glycerol | 15 % |
| Benzylidene-camphor | 3 % |
| Compound no. 10 | 1 % |
| Triethanolamine q.s.p. | pH 7 |
| Water q.s.p. | 100 g % |

An analogous result is obtained by adding lactic acid, in an amount of 1%, to the above anti-sunburn milk.

EXAMPLE A₄: The following anti-sunburn milk is prepared:

| Sipol wax | 5 % |
|---|---|
| Vaseline oil | 6 % |
| Isopropyl palmitate | 3 % |
| Silicone oil | 1 % |
| Cetyl alcohol | 1 % |
| Glycerol | 10 % |
| 3-(4'-Octyloxymethylbenzylidene)-camphor | 2.8 % |
| Compound no. 19 | 3 % |
| N,N'-Bis-(2-hydroxyethyl)-piperazine | 1.3 % |
| Water q.s.p. | 100 g % |

B. COMPOSITIONS OF ANTI-SUNBURN CREAMS:

EXAMPLE B₁: The following non-ionic protective cream is prepared:

| Sipol wax | 7 %/g |
|---|---|
| Glycerol monostearate | 2 %/g |
| Vaseline oil | 15 %/g |
| Silicone oil | 1.5 %/g |
| Cetyl alcohol | 1.5 %/g |
| Preservative | 0.3 %/g |
| Glycerol | 10 %/g |
| Compound no. 18 | 5 %/g |
| Perfume | 0.5 %/g |
| Water q.s.p. | 100 %/g |

The same cream base can be used to prepare a composition for sensitive skin, by adding 2 g of 4-(2-oxobornylidene-3-methyl)-phenyltrimethylammonium methylsulphate or by combining 2.5 g of compound no. 18 with 4 g of the abovementioned methylsulphate.

EXAMPLE B₂: The following anionic protective cream is prepared:

| Self-emulsifiable glycerol monostearate | 6 %/g |
|---|---|
| Polyoxyethyleneated sorbitan monostearate containing 60 mols of ethylene oxide | 2 %/g |
| Stearic acid | 2 %/g |
| Cetyl alcohol | 1.2 %/g |
| Lanoline | 4 %/g |

-continued

| | |
|---|---|
| Vaseline oil | 30 %/g |
| Preservative | 0.3 %/g |
| Compound no. 10 | 4 %/g |
| Triethanolamine | pH 7.5 |
| Perfume | 0.5 %/g |
| Water | 100 %/g |

Analogous results are obtained by adding 1.5% of sodium pyrrolidonecarboxylate to the abovementioned cream.

EXAMPLE B3: The following high-protection sun cream is prepared:

| | |
|---|---|
| Polyoxyethyleneated hydrogenated palm oil | 5 %/g |
| Cetyl/stearyl alcohol containing 15 mols of ethylene oxide | 5 %/g |
| Lanoline | 3 %/g |
| Lanoline alcohols | 1 %/g |
| Sunflower oil | 5 %/g |
| Vaseline oil | 10 %/g |
| 4-(2-Oxobornylidene-3-methyl)-phenyl-trimethylammonium methylsulphate | 2.5 %/g |
| Compound no. 3 | 3.5 %/g |
| Propylene glycol | 5 %/g |
| Perfume | 0.5 %/g |
| Water q.s.p. | 100 %/g |

EXAMPLE B4: The following anti-sunburn cream is prepared:

| | |
|---|---|
| Cetyl/stearyl alcohol | 2 %/g |
| Glycerol monostearate | 4 %/g |
| Cetyl alcohol | 4 %/g |
| Vaseline oil | 5 %/g |
| Butyl stearate | 5 %/g |
| Propylene glycol | 7 %/g |
| Silicon oil | 0.125 %/g |
| 0.5 % strength polyox | 3.5 %/g |
| Preservative | 0.3 %/g |
| Perfume | 0.4 %/g |
| 2-Methyl-5-(2-oxobornylidene-3-methyl)-benzenesulphonic acid | 2.0 %/g |
| Compound no. 5 | 2.5 %/g |
| Water q.s.p. | 100 ml |

EXAMPLE B5: The following high-protection tinted sun cream is prepared:

| | |
|---|---|
| Polyoxyethyleneated hydrogenated palm oil | 5 %/g |
| Cetyl/stearyl alcohol | 5 %/g |
| Lanoline | 3 %/g |
| Lanoline alcohols | 1 %/g |
| Sunflower oil | 5 %/g |
| Vaseline oil | 10 %/g |
| Compound no. 8 | 4 %/g |
| 4-(2-Oxobornylidene-3-methyl)-phenyltrimethyl-ammonium methylsulphate | 2 %/g |
| Propylene glycol | 5 %/g |
| Iron oxide | 0.2 %/g |
| Perfume | 0.5 %/g |
| Water q.s.p. | 100 %/g |

EXAMPLE B6: The following tinted protective cream is prepared:

| | |
|---|---|
| Sipol wax | 6 %/g |
| Glycerol monostearate | 2 %/g |
| Vaseline oil | 13 %/g |
| Silicone oil | 1.5 %/g |
| Cetyl alcohol | 1.5 %/g |
| Iron oxide | 0.01 %/g |
| Preservative | 0.3 %/g |

-continued

| | |
|---|---|
| Glycerol | 12 %/g |
| Compound no. 18 | 3.5 %/g |
| Perfume | 0.5 %/g |
| Water q.s.p. | 100 %/g |

C. EXAMPLES OF ANTI-SUNBURN LOCATIONS

EXAMPLE C1: The following oily-alcoholic anti-sunburn lotion is prepared:

| | |
|---|---|
| Lanoline | 2.5 %/g |
| Triglycerides of $C_8$–$C_{12}$ fatty acids | 40 %/g |
| Perfume | 1.25 %/g |
| Preservatives | 0.3 %/g |
| Compound no. 7 | 4 %/g |
| 96° strength alcohol q.s.p. | 100 g/% |

EXAMPLE C2: The folowing anti-sunburn lotion is prepared:

| | |
|---|---|
| Glycerol | 5 %/g |
| Polyethylene glycol 400 | 0.5 %/g |
| Oxyethyleneated lanoline | 1 %/g |
| Soluble perfume | 2 %/g |
| Compound no. 35 | 6 %/g |
| 96° strength alcohol | 50 %/g |
| Water q.s.p. | 100 %/g |

D. EXAMPLE OF AEROSOL FOAM

EXAMPLE D1: The following aerosol foam is prepared:

| | |
|---|---|
| Sipol wax | 3.5 %/g |
| Vaseline oil | 6 %/g |
| Isopropyl myristate | 3 %/g |
| Preservative | 0.3 %/g |
| Glycerol | 10 %/g |
| Compound no. 20 | 4.5 %/g |
| Water q.s.p. | 100 %/g |

A usual propellant, such as optionally fluorinated or chlorofluorinated hydrocarbons, is used as the propellant, in an amount of about 15 g per 100 g of composition.

E. EXAMPLE OF SPRAY:

EXAMPLE E1: The following anti-sunburn spray is prepared:

| | |
|---|---|
| Absolute alcohol | 30 %/g |
| Isopropyl myristate | 20 %/g |
| Castor oil | 2 %/g |
| Lanoline | 5 %/g |
| Perfume | 1 %/g |
| Compound no. 18 | 3 %/g |
| Freon 12 | 40 %/g |

F. EXAMPLES OF SUN OILS:

EXAMPLE F1: The following anti-sunburn oil is prepared:

| | |
|---|---|
| Cocoa butter | 2.5 %/g |
| Compound no. 8 | 1.5 %/g |
| 3-(4'-Hexanoyloxybenzylidene)-bornan-2-one | 2 %/g |
| Butylhydroxyanisole | 0.05 %/g |
| Perfume | 0.5 %/g |

-continued

| Vegetable oil | 100 %/g |

EXAMPLE F₂: The following sun oil is prepared:
| Lanoline | 2.5 %/g |
| Butylhydroxyanisole | 0.1 %/g |
| Compound no. 18 | 2 %/g |
| 3-(4'-Tetradecanoyloxybenzylidene)-bornan-2-one | 1 %/g |
| Perfume | 0.5 %/g |
| Triglycerides of C₈-C₁₂ fatty acids q.s.p. | 100 %/g |

EXAMPLE F₃: The following sun oil is prepared:
| Lanoline | 2.5 %/g |
| 3-(4'-Oleyloxymethylbenzylidene)-camphor | 3 %/g |
| Compound no. 18 | 3 %/g |
| Butylhydroxyanisole | 0.05 %/g |
| Perfume | 0.5 %/g |
| Triglycerides of C₈-C₁₂ fatty acids q.s.p. | 100 %/g |

Similar results can be obtained by replacing the compounds of formula (I) by other compounds as follows:

| Example | Compound | Concentration |
|---------|----------|---------------|
| A1 | 12 | 3% |
| A3 | 11 | 1.5% |
| A4 | 32 | 3% |
| *B1 | 4 | 5% |
| +B2 | 13 | 6% |
|  | 19 | 4% |
| B3 | 5 | 4% |
| B6 | 14 (Mg salt) | 4.3% |
| C1 | 6 | 4% |
| C2 | 33 | 3.5% |
|  | 33 | 3.5% + 2.5% benzylidene-camphor |
| E1 | 6 | 3% |

*adjusting the pH to 5 with lactic acid
+adjusting the pH to 6 with triethanolamine

We claim:
1. Compound having the general formula:

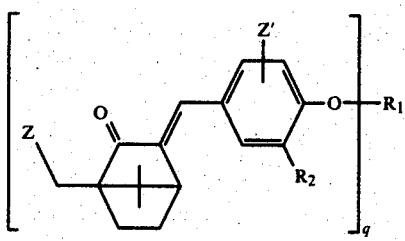

in which: Z and Z' independently denote a hydrogen atom or a SO₃H radical or a salt thereof with an inorganic or organic base, at least one of Z and Z' denoting a hydrogen atom; R₁ denotes a hydrogen atom, an alkyl radical containing 2 to 18 carbon atoms when R₂ is other than an alkoxy radical, an alkyl radical containing 1 to 18 carbon atoms when R₂ is an alkoxy radical, an alkenyl radical containing 3 to 18 carbon atoms, a radical of formula $$-(CH_2CH_2O)_nH, \quad -(CH_2-CH-O)_nH,$$
$$\qquad\qquad\qquad\qquad\qquad |$$
$$\qquad\qquad\qquad\qquad\qquad CH_3$$

$$-(CH_2-CHO)_pH, \quad -CH-CHOH-CH_3,$$
$$\qquad |$$
$$\qquad CH_2OH$$

$$-CH_2-CH_2-N\begin{matrix}R_3\\ \diagup\\ \diagdown\\ R_4\end{matrix}, \quad -CH_2-CHOH-CH_2-N\begin{matrix}R_3\\ \diagup\\ \diagdown\\ R_4\end{matrix},$$

$$-(CH_2)_3-SO_3H$$

or a salt thereof with an organic or inorganic base, or $-(CH_2)_mCO_2R$, in which R denotes H or an alkyl radical containing 1 to 8 carbon atoms, or a divalent radical of formula $-(CH_2)_m-$ or $-CH_2-CHOH-CH_2$, m having a value from 1 to 10, n having a value from 1 to 20 and p having a value from 1 to 6, and R₃ and R₄ each independently denote a hydrogen atom or an optionally branched or hydroxy alkyl radical, or R₃ and R₄ together form a morpholino or a piperidino ring with the nitrogen atom to which they are attached; R₂ denotes a hydrogen atom, an alkoxy radical containing 1 to 4 carbon atoms or a divalent radical $-O-$ bonded to the radical R₁ if the latter is also divalent; q denotes 1 or 2, such that if q is 2, R₁ is a said divalent radical, with the proviso that if R₁ denotes hydrogen R₂ also denotes hydrogen; when q is 1, at least one of Z, Z', R₁ and R₂ is not hydrogen and when Z and Z' are both hydrogen, R₁ is not $-CH_2-$ when R₂ is $-O-$.

2. Compound according to claim 1 in which Z' denotes hydrogen, q is 1 and R₁ is not hydrogen.
3. Compound according to claim 1 in which Z' denotes hydrogen, q is 2 and R₁ is not hydrogen.
4. Compound according to claim 1 in which Z' denotes the radical SO₃H or a salt thereof.
5. 3-(3',4'-Dimethoxybenzylidene)-bornan-2-one.
6. 3-[4'-(2,3-Dihydroxypropoxy)-benzylidene]-bornan-2-one.
7. 3-(4'-Butoxy-3'-methoxybenzylidene)-2-oxobornane-10-sulphonic acid.
8. 3-(4'-Butoxybenzylidene)-bornan-2-one.
9. Sodium 2-butoxy-5-(2-oxobornylidene-3-methyl)-benzene-sulphonate.
10. 3-(4'-allyloxybenzylidene)-bornan-2-one.

* * * * *